US012076214B2

(12) United States Patent
Hosey et al.

(10) Patent No.: US 12,076,214 B2
(45) Date of Patent: Sep. 3, 2024

(54) MEDICAL PAD

(71) Applicants: Crystal Hosey, Acworth, GA (US);
Tyree Blake, Acworth, GA (US)

(72) Inventors: Crystal Hosey, Acworth, GA (US);
Tyree Blake, Acworth, GA (US)

(*) Notice: Subject to any disclaimer, the term of this patent is extended or adjusted under 35 U.S.C. 154(b) by 71 days.

(21) Appl. No.: 17/566,640

(22) Filed: Dec. 30, 2021

(65) Prior Publication Data

US 2022/0202621 A1   Jun. 30, 2022

Related U.S. Application Data

(60) Provisional application No. 63/132,416, filed on Dec. 30, 2020.

(51) Int. Cl.
*A61F 13/02*      (2024.01)
*A61F 13/00*      (2024.01)

(52) U.S. Cl.
CPC .... *A61F 13/02* (2013.01); *A61F 2013/00404* (2013.01); *A61F 2013/00587* (2013.01); *A61F 2013/00655* (2013.01); *A61F 2013/00855* (2013.01)

(58) Field of Classification Search
CPC .... A61F 13/02; A61F 13/023; A61F 13/0243; A61F 2013/00404; A61F 2013/00587; A61F 2013/00655; A61F 2013/00855; A61F 2013/00702; A61F 2013/00859; A61F 2013/00863; A61F 2013/00246; A61F 2013/00251; A61F 2013/00255; A61F 2013/00582; A61F 13/00; A61F 13/00008; A61F 13/00021; A61F 13/069; A61F 13/06; A61F 13/063

USPC ............. 128/889–894; 602/41, 47, 58, 59
See application file for complete search history.

(56) References Cited

U.S. PATENT DOCUMENTS

| | | | | |
|---|---|---|---|---|
| 2,785,677 | A  * | 3/1957 | Stumpf | A61F 13/0206 |
| | | | | 602/58 |
| 7,175,502 | B2 * | 2/2007 | Clark | A61F 13/141 |
| | | | | 128/889 |
| 8,686,214 | B2 * | 4/2014 | Hyde-Edwards | A61F 13/141 |
| | | | | 602/61 |
| 2010/0174250 | A1 * | 7/2010 | Hu | A61F 13/0216 |
| | | | | 602/54 |

(Continued)

FOREIGN PATENT DOCUMENTS

CN    202982403 U  *  6/2013
RU    2615075 C2  *  4/2017   ....... A61F 13/00029

OTHER PUBLICATIONS

Machine translation of CN 202982403 U (Year: 2013).*
Machine translation of RU 2615075 C2 (Year: 2017).*

*Primary Examiner* — Caitlin A Carreiro
(74) *Attorney, Agent, or Firm* — Incorporating Innovation LLC; Charlena Thorpe, Esq.

(57) ABSTRACT

Implementations of a medical pad having a perimeter side, a first surface, a second surface, and a plurality of openings. In some implementations, a method of using the medical pad includes positioning the medical pad on an area susceptible to the development of a bedsore or similar wound, such as a bony prominence or pressure point, to prevent the development of a bedsore or similar wound, and another method includes positioning the medical pad on a bedsore or similar wound to help the treatment and healing of the bedsore or similar wound.

16 Claims, 10 Drawing Sheets

(56) References Cited

U.S. PATENT DOCUMENTS

2011/0165221 A1\* 7/2011 Jung .................. A61L 26/0085
424/673
2017/0056251 A1\* 3/2017 Mack ................. A61F 13/0253

\* cited by examiner

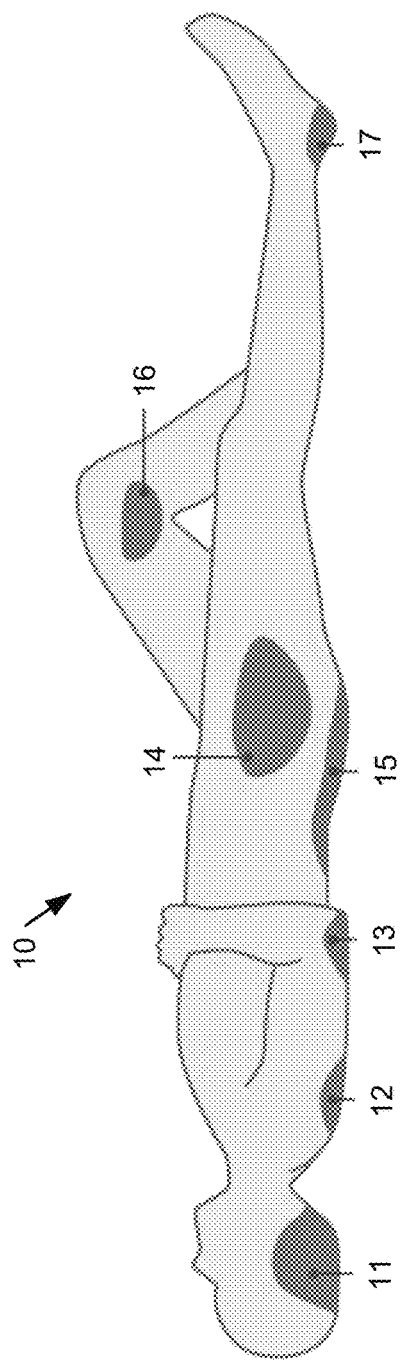
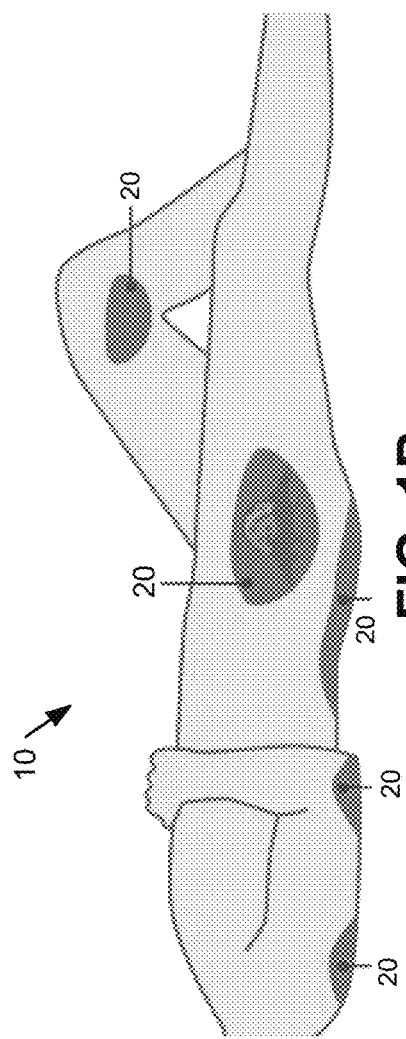
FIG. 1A (PRIOR ART)
FIG. 1B (PRIOR ART)

MEDICAL PAD

CROSS REFERENCE TO RELATED APPLICATION

This application claims the benefit of U.S. Patent Application Ser. No. 63/132,416, which was filed on Dec. 30, 2020, and is incorporated herein by reference in its entirety.

TECHNICAL FIELD

This disclosure relates to implementations of a medical pad that prevents the development of bed sores and helps the treatment and healing of existing bed sores.

BACKGROUND

Many people are affected by skin breakdown that causes the development of pressure ulcers also known as bed sores (or bedsores). As shown in FIG. 1A, such skin breakdown usually results from restricted (e.g., low or loss of) circulation to bony prominences or pressure points of the body, such as the back of the head, shoulder, elbow, hip, lower back, inner knee, or heel. Such restricted circulation is usually due to prolonged lying or sitting in one position (e.g., from being bedridden or wheelchair bound), illness, or weight loss. As shown in FIG. 1B, the skin breakdown from the restricted circulation results in the development of bed sores (or pressure ulcers).

There are existing products designed to help treat or heal bed sores, but these products do not help prevent the development of bed sores. For example, silicon gel bandages exist that can be placed on bed sores for treatment or healing. There are also existing products designed to help prevent the development of bed sores, but these products cannot be used directly on the skin and do not help the treatment or healing of bed sores. For example, pads exist that can be placed on a bed to help prevent the development of bed sores, but these pads are not intended to be placed directly on the skin and do not help the treatment or healing of bed sores. Therefore, a product does not exist that prevents the development of bed sores and can be used directly on the skin and that also helps the treatment and healing of existing bed sores.

BRIEF DESCRIPTION OF THE DRAWINGS

FIG. 1A illustrates examples of skin breakdown on a body.

FIG. 1B illustrates an example of pressure ulcers or bed sores on a body.

DETAILED DESCRIPTION

Figure 2A:
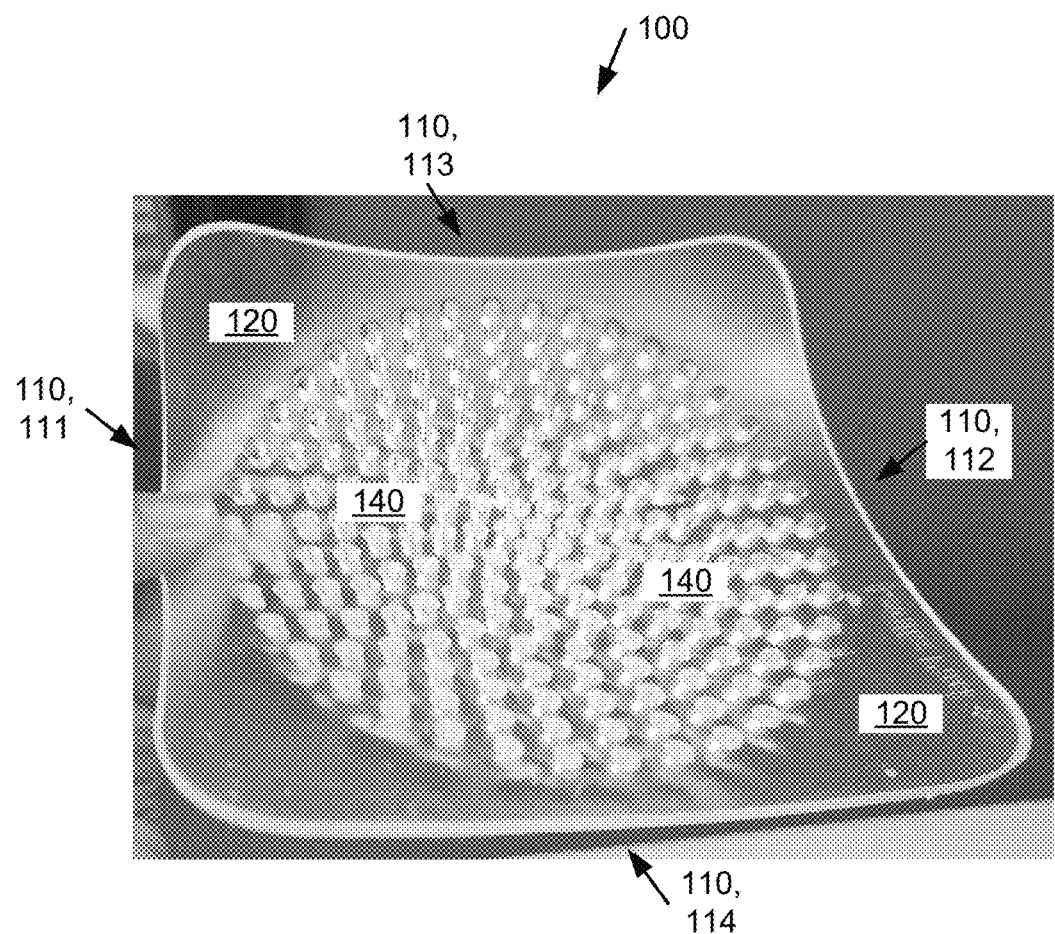
FIGS. 2A-2D illustrate an implementation of an example medical pad according to the present disclosure.

Implementations of a medical pad are provided. In some implementations, the medical pad comprises a perimeter side, a first surface, a second surface, and a plurality of openings.

In some implementations, the medical pad is configured to prevent the development of pressure ulcers or bed sores (or bedsores).

In some implementations, the medical pad is configured to help the treatment and/or healing of existing bed sores.

In some implementations, the medical pad is configured to reduce or prevent skin breakdown that causes the development of bed sores.

In some implementations, the medical pad is configured to allow existing bed sores to heal.

In some implementations, the medical pad is configured to allow a user's skin to breath when the medical pad is used.

In some implementations, the medical pad is configured to use for preventive care of bony prominences or pressure points of a user's body to prevent skin breakdown and the development of bed sores.

In some implementations, the medical pad is configured to prevent restriction of circulation that causes skin breakdown and the development of bed sores.

In some implementations, the medical pad is configured to act as a shock absorber to pressure points of a user.

In some implementations, the medical pad is configured to reduce pain related to fat buildup.

In some implementations, the medical pad is configured to reduce pain related to muscle deterioration.

In some implementations, the medical pad is configured to reduce or alleviate other pain related to the treatment, healing, and/or prevention of bedsores or similar wounds.

In some implementations, the medical pad is configured to help to protect a wound.

In some implementations, the medical pad is configured to safely and effectively use in direct contact with a user's skin.

In some implementations, the medical pad is configured to adhere to a user's skin or a covered wound.

In some implementations, the medical pad is configured to re-adhere to a user's skin or a covered wound after previously adhering and removing the medical pad.

In some implementations, the medical pad is configured to re-adhere to a user's skin or a covered wound after previously adhering, removing, and washing or otherwise cleaning the medical pad.

In some implementations, a method of using the medical pad comprises positioning the medical pad on an area susceptible to the development of a bedsore or similar wound, such as a bony prominence or pressure point, to prevent the development of a bedsore or similar wound. In some implementations, a method of using the medical pad comprises positioning the medical pad on a bedsore or similar wound to help the treatment and healing of the bedsore or similar wound.

Many people are affected by skin breakdown that causes the development of pressure ulcers also known as bed sores (or bedsores). As shown in FIG. 1A, such skin breakdown usually results from restricted (e.g., low or loss of) circulation to bony prominences or pressure points of the body 10, such as the back of the head 11, shoulder 12, elbow 13, hip 14, lower back 15, inner knee 16, or heel 17. Such restricted circulation is usually due to prolonged lying or sitting in one position (e.g., from being bedridden or wheelchair bound), illness, or weight loss. As shown in FIG. 1B, the skin breakdown from the restricted circulation results in the development of bed sores (or pressure ulcers) 20.

There are existing products designed to help treat or heal bed sores, but these products do not help prevent the development of bed sores. For example, silicon gel bandages exist that can be placed on bed sores for treatment or healing. There are also existing products designed to help prevent the development of bed sores, but these products cannot be used directly on the skin and do not help the treatment or healing of bed sores. For example, pads exist that can be placed on a bed to help prevent the development of bed sores, but these pads are not intended to be placed directly on the skin and do not help the treatment or healing of bed sores. Therefore, a product does not exist that prevents the development of bed sores and also helps the treatment and healing of existing bed sores.

Figure 2B:
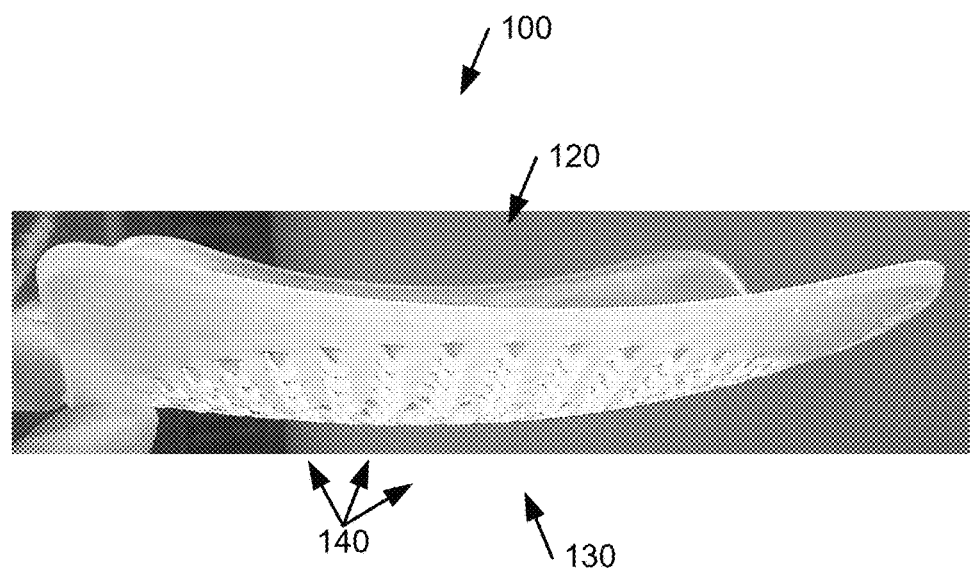
Figure 2C:
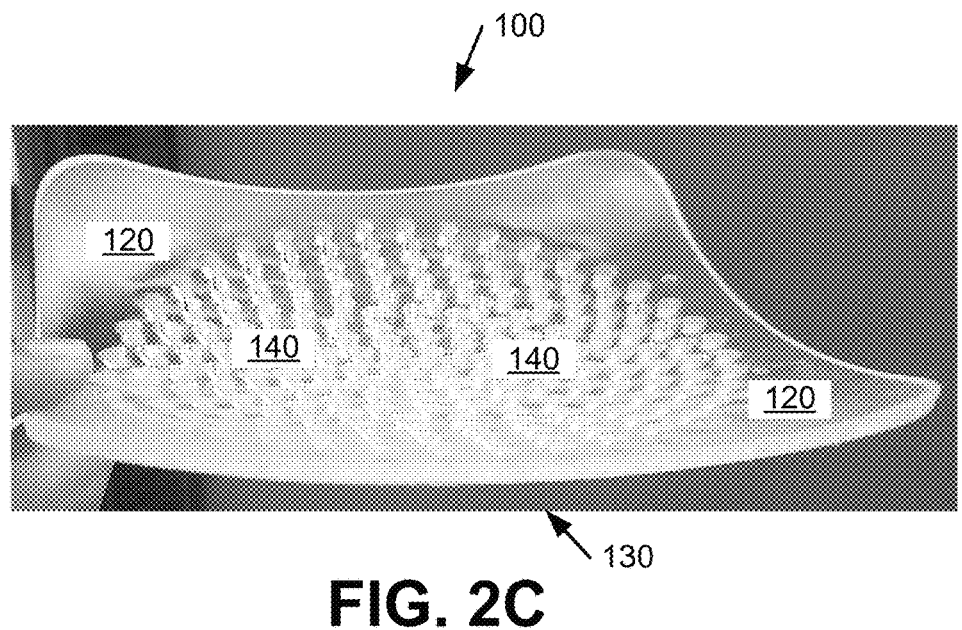

FIGS. 2A-2D illustrate an implementation of an example medical pad 100 according to the present disclosure. As shown in FIGS. 2A and 2B, in some implementations, the medical pad 100 comprises a perimeter side 110, a first surface 120, a second surface 130, and a plurality of openings 140. For example, in some implementations, the medical pad 100 is a piece of material, such as the example material described below, having these components 110, 120, 130, 140.

In some implementations, the medical pad 100 may comprise any other suitable components.

Figure 6A:
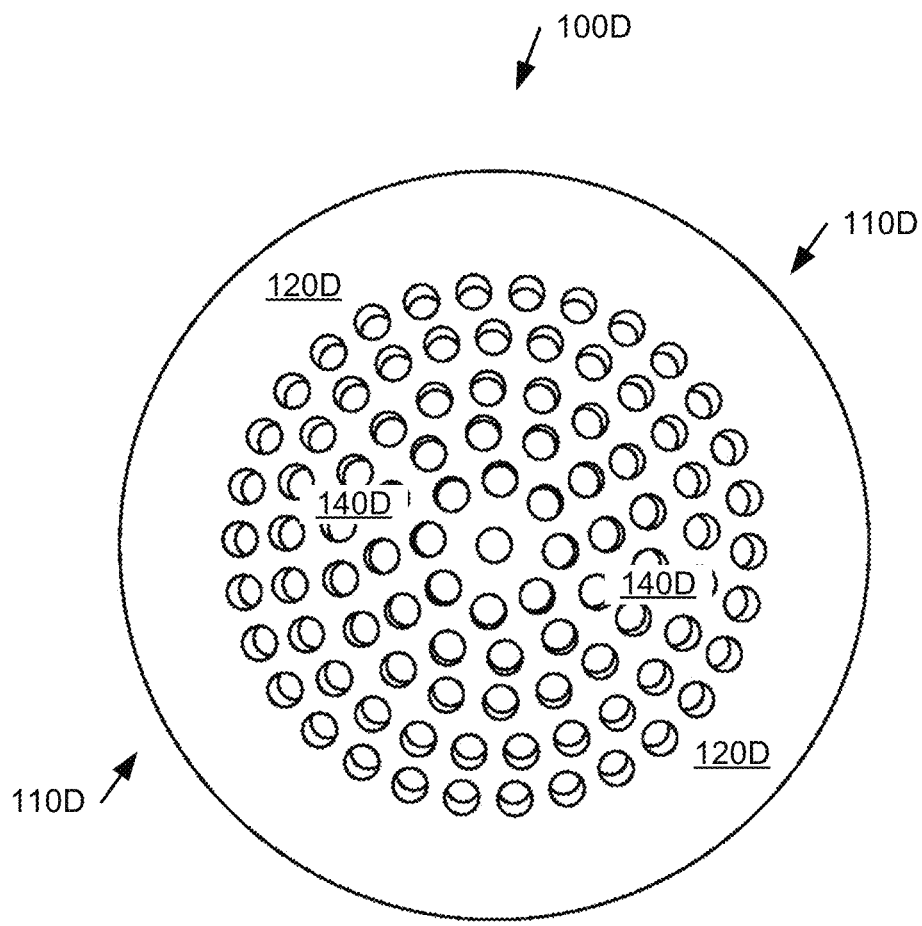
FIGS. 6A and 6B illustrate another implementation of an example medical pad according to the present disclosure.
Figure 7:
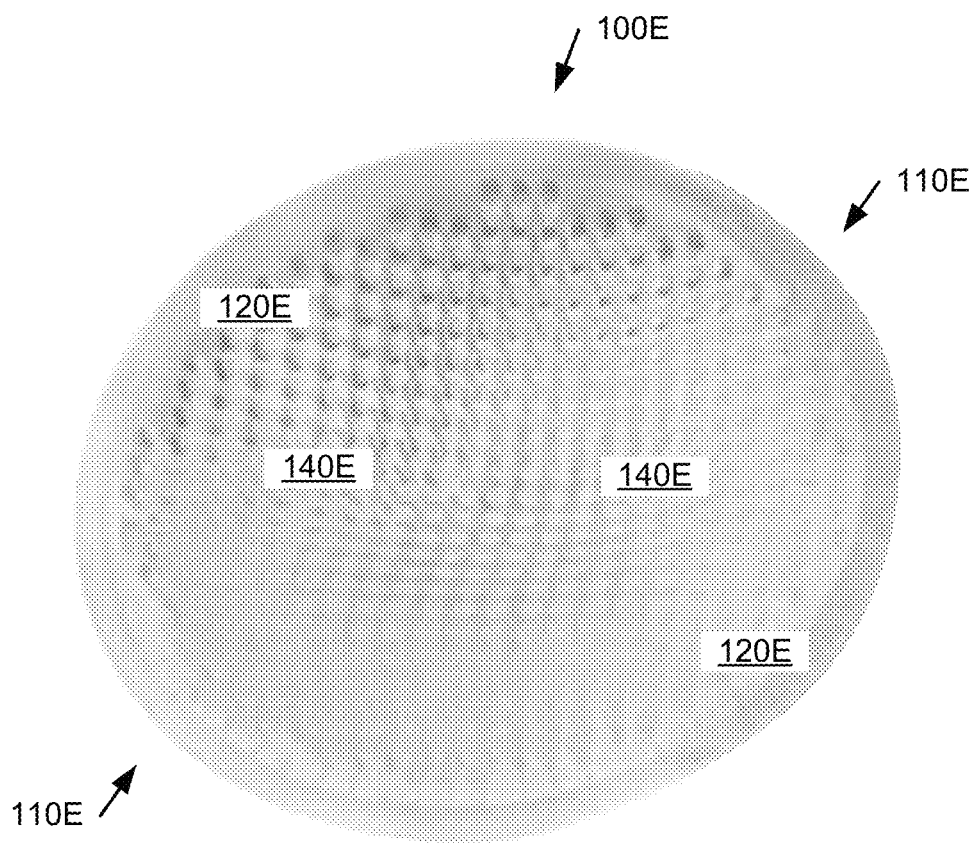
FIG. 7 illustrates another implementation of an example medical pad according to the present disclosure.

In some implementations, the perimeter side 110 may be any suitable shape. For example, as shown in FIG. 2A, in some implementations, the perimeter side 110 may be generally square or rectangular shaped and comprise a plurality of sides 111, 112, 113, 114. As shown in FIGS. 6A and 7 (described more below), in some implementations, the perimeter side 110 may be generally curved or circular shaped.

As shown in FIG. 2A, in some implementations, for the generally rectangular shaped perimeter side 110, a generally opposite first side 111 and second side 112 extend respectively between a generally opposite third side 113 and fourth side 114. Similarly, in some implementations, the generally opposite third side 113 and fourth side 114 extend respectively between the generally opposite first side 111 and second side 112.

Figure 2D:
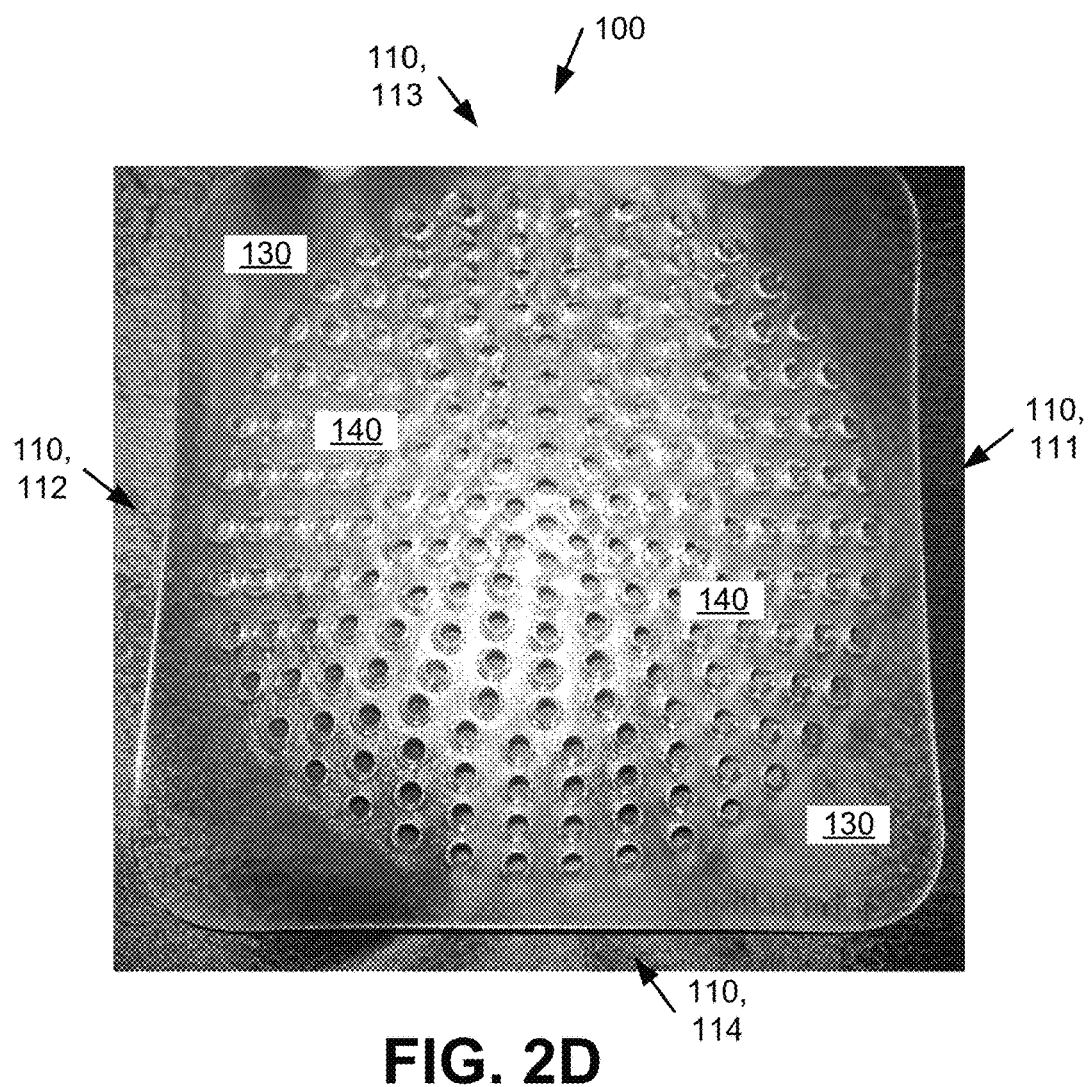

In some implementations, the first surface 120 and the second surface 130 may each be any suitable shape. In some implementations, the surfaces 120, 130 are the same or similar shape. For example, as shown in FIGS. 2A and 2D, in some implementations, the surfaces 120, 130 may be generally square or rectangular shaped. As shown in FIGS. 6A and 7 (described more below), in some implementations, the surfaces 120, 130 may be generally curved or circular shaped.

As shown in FIGS. 2A and 2D, in some implementations, the generally rectangular shaped surfaces 120, 130 extend generally opposite respectively (e.g., lengthwise) between the first side 111 and the second side 112. Similarly, in some implementations, the generally rectangular shaped surfaces 120, 130 extend generally opposite respectively (e.g., widthwise) between the third side 113 and fourth side 114.

As shown in FIGS. 6A and 7, in some implementations, the generally circular shaped surfaces 120, 130 extend generally opposite respectively (e.g., widthwise or radially) between the perimeter side 110.

As shown in FIGS. 2B and 2C and FIGS. 3A and 6B (described more below), in some implementations, the surfaces 120, 130 also extend in a generally curved shape between the perimeter side 110. For example, in some implementations, the surfaces 120, 130 extend generally parallel in a generally concave, convex, and/or similar shape.

In some implementations, the surfaces 120, 130 extend generally curved such that the first surface 120 extends concave (e.g., concave inward) toward the second surface 130 and the second surface 130 extends concave (e.g., concave outward or convex) away from the first surface 120. In some implementations, the surfaces 120, 130 thereby have a concave (e.g., depression, teardrop, etc.) shaped portion as the surfaces 120, 130 extends from the perimeter side 110.

In some implementations, the concave shaped portion is configured (e.g., sized and shaped) to position on or over (e.g., in contact with or not in contact with) a bedsore or similar wound (e.g., for treatment and/or healing) or an area susceptible to the development of a bedsore or similar wound (e.g., for prevention).

Figure 6B:
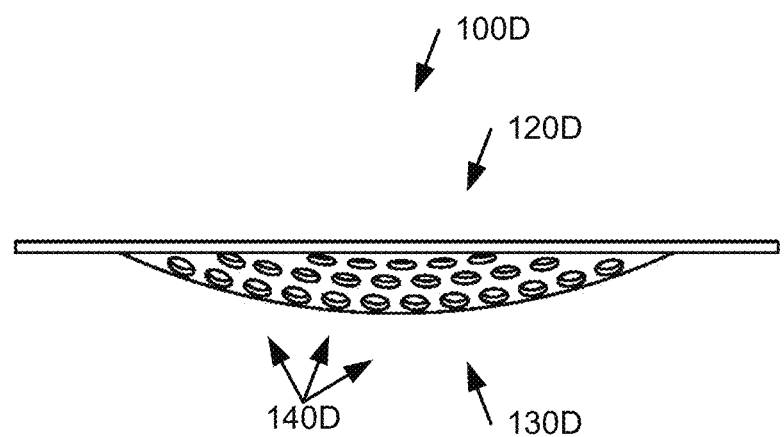

As shown in FIG. 6B, in some implementations, the surfaces 120, 130 may extend generally straight or flat from the perimeter side 110. For example, in some implementations, the surfaces 120, 130 may extend generally flat and then generally concave, convex, etc. as described above.

In some implementations, the surfaces 120, 130 may extend in any other suitable between the perimeter side 110.

In some implementations, the first surface 120 is configured to be positioned on or adjacent to a user's skin (or bedsore, skin wound, etc.) when the medical pad 100 is used. In some implementations, the first surface 120 is configured to thereby face toward the user's skin when the medical pad 100 is used.

In some implementations, the first surface 120 may be configured to be positioned in any other suitable way when the medical pad 100 is used.

In some implementations, the second surface 130 is configured to be positioned opposite or away from a user's skin (or bedsore, skin wound, etc.) when the medical pad 100 is used. In some implementations, the second surface 130 is configured to thereby face away from the user's skin when the medical pad 100 is used.

In some implementations, the second surface 130 may be configured to be positioned in any other suitable way when the medical pad 100 is used.

In some implementations, the openings 140 may comprise any suitable number of openings. For example, in some implementations, the openings 140 may comprise two or more openings. In some implementations, the openings 140 may comprise one opening.

In some implementations, the openings 140 may be any suitable shape. For example, as shown in FIG. 2D, in some implementations, the openings 140 may be generally circular and/or cylindrical.

Figure 5A:
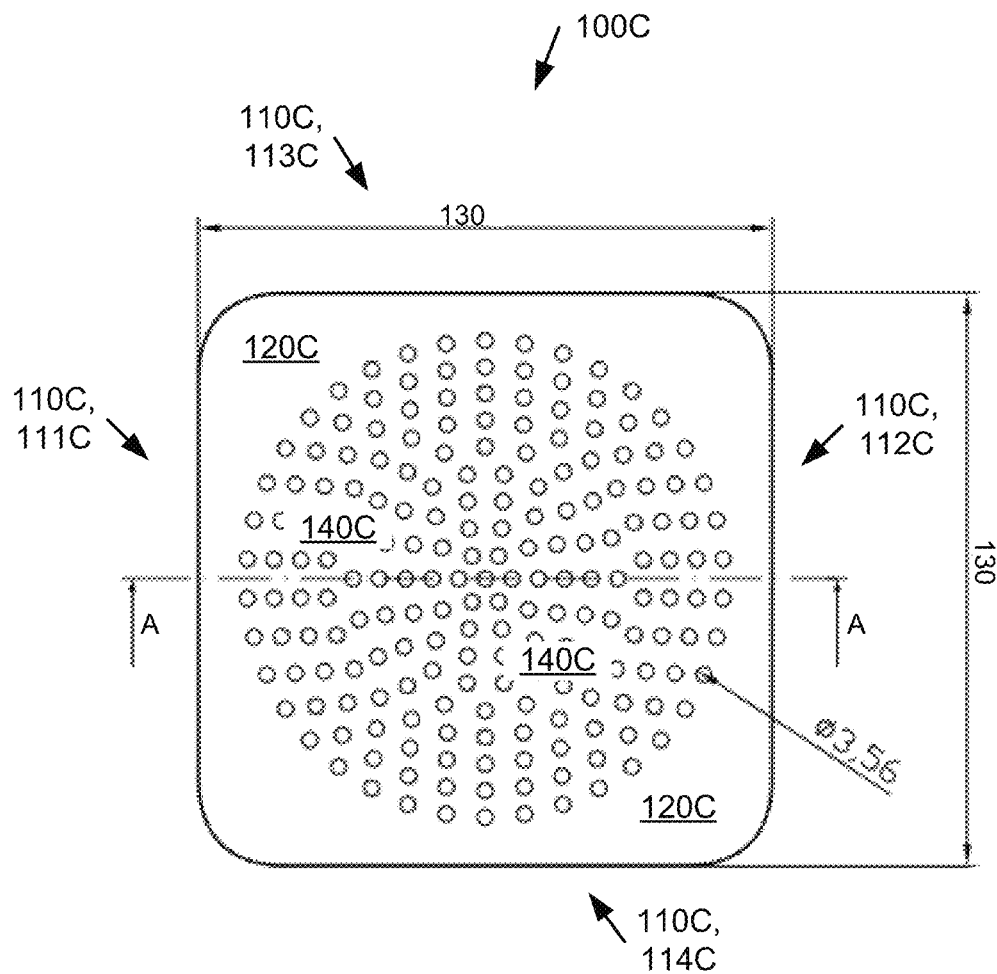
FIGS. 5A and 5B illustrate example dimensions of the medical pad according to the present disclosure.

In some implementations, the openings 140 may be any suitable size. For example, as shown in FIG. 5A, in some implementations, the openings 140 may be 3.56 millimeters in width or diameter. In some implementations, the openings 140 may be greater than or less than 3.56 millimeters in width.

As shown in FIGS. 2A and 2D and FIGS. 3B, 3C, 5B, 6A, and 6B (described more below), in some implementations, the openings 140 extend between the first surface 120 and the second surface 130. In some implementations, the openings 140 extend between and through the first surface 120 and the second surface 130.

In some implementations, the openings 140 extend in a honeycomb (or similar) pattern or configuration. For example, in some implementations, the openings 140 extend adjacently in a honeycomb or similar configuration.

In some implementations, the openings 140 may extend in any other suitable way.

In some implementations, the openings 140 are configured to allow a user's skin, bedsore, wound, etc. to breathe when the medical pad 100 is used. For example, in some implementations, the openings 140 are configured (e.g., sized and shaped) to allow air, vapor, etc. to pass through the openings 140.

In some implementations, the openings 140 are configured to provide any other suitable features.

In some implementations, the medical pad 100 may be any suitable shape. For example, as shown in FIGS. 2A and 2B, in some implementations, the medical pad 100 may be generally square or rectangular shaped along the perimeter side 110 and generally curved or concave shaped (as described above) along the surfaces 120, 130. As shown in FIGS. 6A and 6B, in some implementations, the medical pad 100 may be generally curved or circular shaped along the perimeter side 110 and generally curved or concave shaped along the surfaces 120, 130.

In some implementations, the medical pad 100 may be any suitable size. For example, in some implementations, the medical pad 100 is sized such that the medical pad 100 can be used to prevent the development of bed sores (or bedsores) and/or to help the treatment and/or healing of existing bed sores.

In some implementations, the medical pad 100 is configured to prevent the development of pressure ulcers or bed sores.

In some implementations, the medical pad 100 is configured to help the treatment and/or healing of existing bed sores.

In some implementations, the medical pad 100 is configured to reduce or prevent skin breakdown that causes the development of bed sores.

In some implementations, the medical pad 100 is configured to allow existing bed sores to heal.

In some implementations, the medical pad 100 is configured to allow a user's skin to breath when the medical pad 100 is used. For example, in some implementations, the honeycomb configuration of the openings 140 allow the user's skin to breath.

In some implementations, the medical pad 100 is configured to use for preventive care of bony prominences or pressure points of a user's body to prevent skin breakdown and the development of bed sores.

In some implementations, the medical pad 100 is configured to prevent restriction of circulation that causes skin breakdown and the development of bed sores.

In some implementations, the medical pad 100 is configured to act as a shock absorber to pressure points (or other applicable areas) of a user. For example, in some implementations, the medical pad 100 is configured to provide shock absorption that protects a bedsore or similar wound or an area susceptible to the development of a bedsore or similar wound from external forces (e.g., from bed laying, obstacle bumping, etc.) which can cause injury or other harm.

In some implementations, the medical pad 100 is configured to reduce (or alleviate) pain when used for the treatment, healing, and/or prevention of bedsores or similar wounds.

For example, in some implementations, the medical pad 100 is configured to reduce pain related to fat buildup. In some implementations, the medical pad 100 is configured to reduce pain related to muscle deterioration.

In some implementations, the medical pad 100 is configured to reduce or alleviate other applicable pain related to the treatment, healing, and/or prevention of bedsores or similar wounds.

In some implementations, the medical pad 100 is configured to help to protect a wound.

In some implementations, the medical pad 100 is configured to safely and effectively use in direct contact with a user's skin.

In some implementations, the medical pad 100 is configured to adhere to a user's skin or a covered wound. For example, in some implementations, the medical pad 100 comprises an adhesive property that allows the medical pad 100 to adhere to the user's skin or a covered wound.

In some implementations, the medical pad 100 is configured to re-adhere to a user's skin or a covered wound after previously adhering and removing the medical pad 100.

In some implementations, the medical pad 100 is configured to re-adhere to a user's skin or a covered wound after previously adhering, removing, and washing or otherwise cleaning the medical pad 100.

In some implementations, the medical pad 100 comprises any suitable dimensions. For example, in some implementations, the medical pad 100 may comprise the same or similar dimensions shown (in millimeters) in FIGS. 5A and 5B.

In some implementations, a generally rectangular shaped medical pad 100, such as shown in FIGS. 2A-2D, may be 5 inches in length and 3 inches in width. In some implementations, the medical pad 100 may be 4 inches in length and 4 inches in width. In some implementations, the medical pad 100 may be 3 inches in length and 3 inches in width.

In some implementations, a generally rectangular shaped medical pad 100 may be 13 centimeters in length, 13 centimeters in width, and 1 centimeter in thickness or depth.

In some implementations, a generally circular shaped medical pad 100, such as shown in FIGS. 6A, 6B, and 7, may be 13 centimeters in diameter.

In some implementations, the medical pad 100 may have a height of 1.5 to 2.5 inches extending generally from the first surface 120 to the second surface 130 including the concave depression of the surfaces 120, 130.

In some implementations, the medical pad 100 may have any other suitable dimensions to use the medical pad 100 on a bony prominence or pressure point of a user to prevent skin breakdown and/or bedsore development.

In some implementations, the medical pad 100 may have any other suitable dimensions to use the medical pad 100 to cover a bedsore or a treated and covered open wound.

In some implementations, the medical pad 100 is composed of any suitable materials. For example, in some implementations, the medical pad 100 is composed of a silicone material. In some implementations, the medical pad 100 is composed of a silicone gel material.

In some implementations, the medical pad 100 is composed of a molded silicone material. In some implementations, the medical pad 100 is composed of a customized silicone material.

In some implementations, the medical pad 100 is composed of a material, such as a silicone material, that includes a mixture or other integration of an adhesive, such as a slight, gentle, or otherwise mild adhesive.

In some implementations, the medical pad 100 is composed of a material that comprises an adhesive property, such as a slight, gentle, or otherwise mild adhesive property.

In some implementations, the medical pad 100 is composed of a material that can adhere to the user's skin or a covered wound.

In some implementations, the medical pad 100 is composed of a material that can re-adhere to a user's skin or a covered wound after previously adhering and removing the medical pad 100.

In some implementations, the medical pad 100 is composed of a material that can re-adhere to a user's skin or a covered wound after previously adhering, removing, and washing or otherwise cleaning the medical pad 100.

In some implementations, the medical pad 100 is composed of a generally lightweight material. For example, in some implementations, a generally rectangular shaped medical pad 100, such as shown in FIGS. 2A-2D, may be composed of a material that weighs 150 grams. In some implementations, the material may weigh less or more than 150 grams.

In some implementations, a generally circular shaped medical pad 100, such as shown in FIGS. 6A, 6B, and 7, may be composed of a material that weighs 100 grams. In some implementations, the material may weigh less or more than 100 grams.

In some implementations, the medical pad 100 may be composed of a material of any other suitable weight.

In some implementations, the medical pad 100 may be composed of a rigid or semi-rigid material. In some implementations, the medical pad 100 may be composed of a flexible or semi-flexible material.

For example, in some implementations, the medical pad 100 may be composed of a material configured such that the medical pad 100 at least partly, fully, etc. maintains its shape, such as when the medical pad 100 is used. In some implementations, the medical pad 100 may be composed of a material having any other suitable rigidity, flexibility, etc.

In some implementations, the medical pad 100 can have any suitable appearance, such as the examples shown in the figures.

Figure 3A:
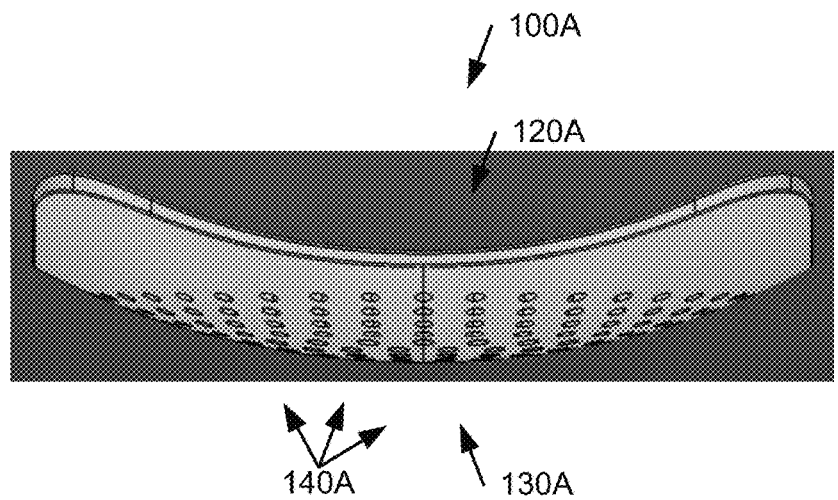
FIGS. 3A-3C illustrate another implementation of an example medical pad according to the present disclosure.
Figure 3B:
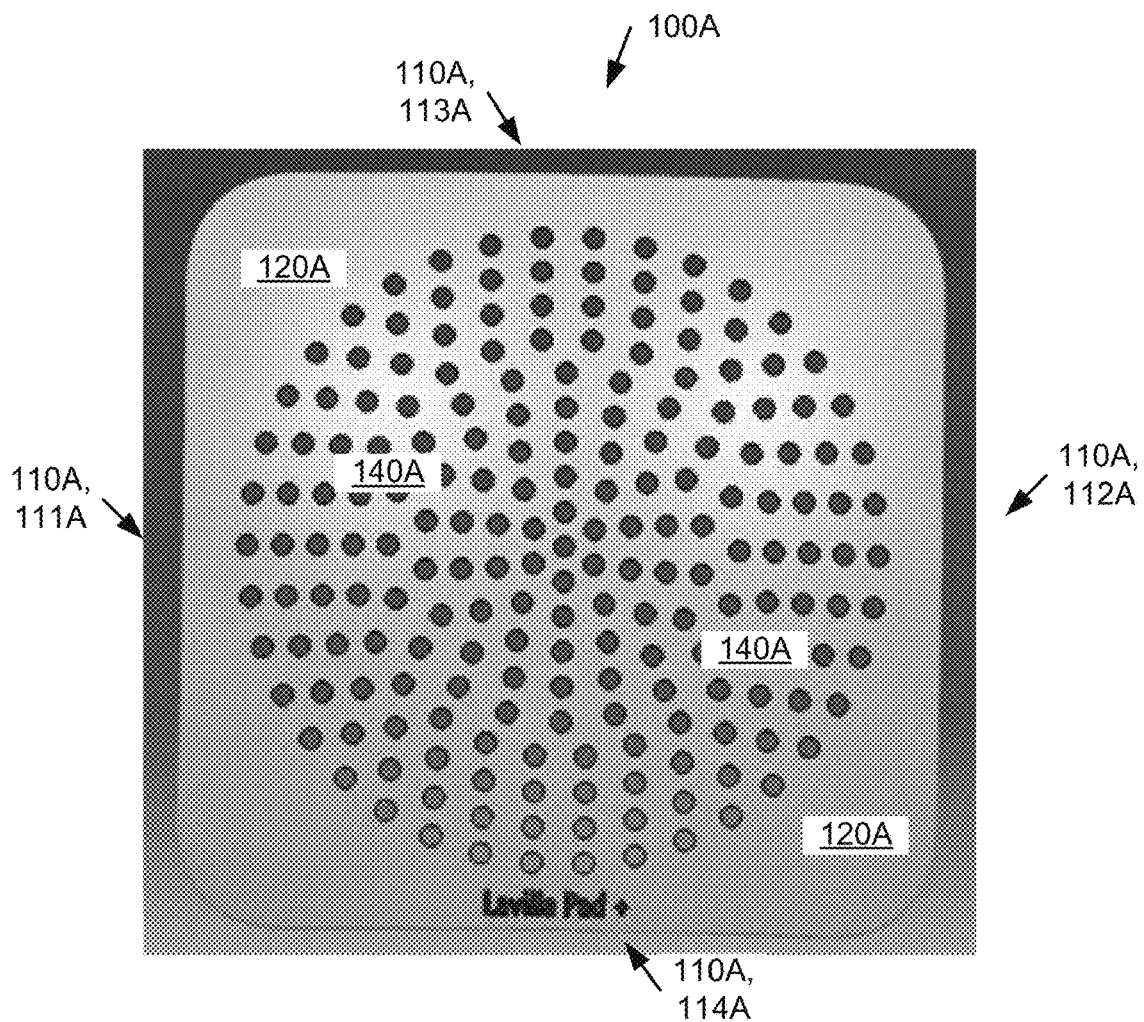
Figure 3C:
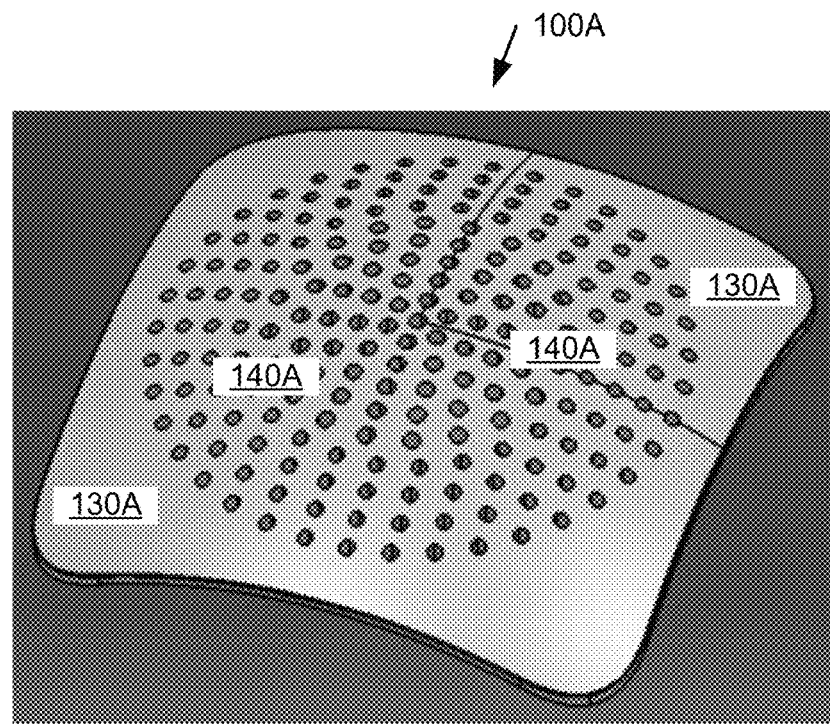

FIGS. 3A-3C illustrate another implementation of an example medical pad 100A according to the present disclosure. In some implementations, the medical pad 100A is generally the same or similar to the medical pad 100 described herein and shown in FIGS. 2A-2D. For example, as shown in FIGS. 3A and 3B, in some implementations, the medical pad 100A comprises a perimeter side 110A, a first surface 120A, a second surface 130A, and a plurality of openings 140A that are generally the same or similar to the perimeter side 110, the first surface 120, the second surface 130, and the plurality of openings 140 of the medical pad 100.

Furthermore, in some implementations, the medical pad 100A is configured to prevent the development of bed sores and to help the treatment and/or healing of existing bed sores the same or similar to the medical pad 100.

Figure 4:
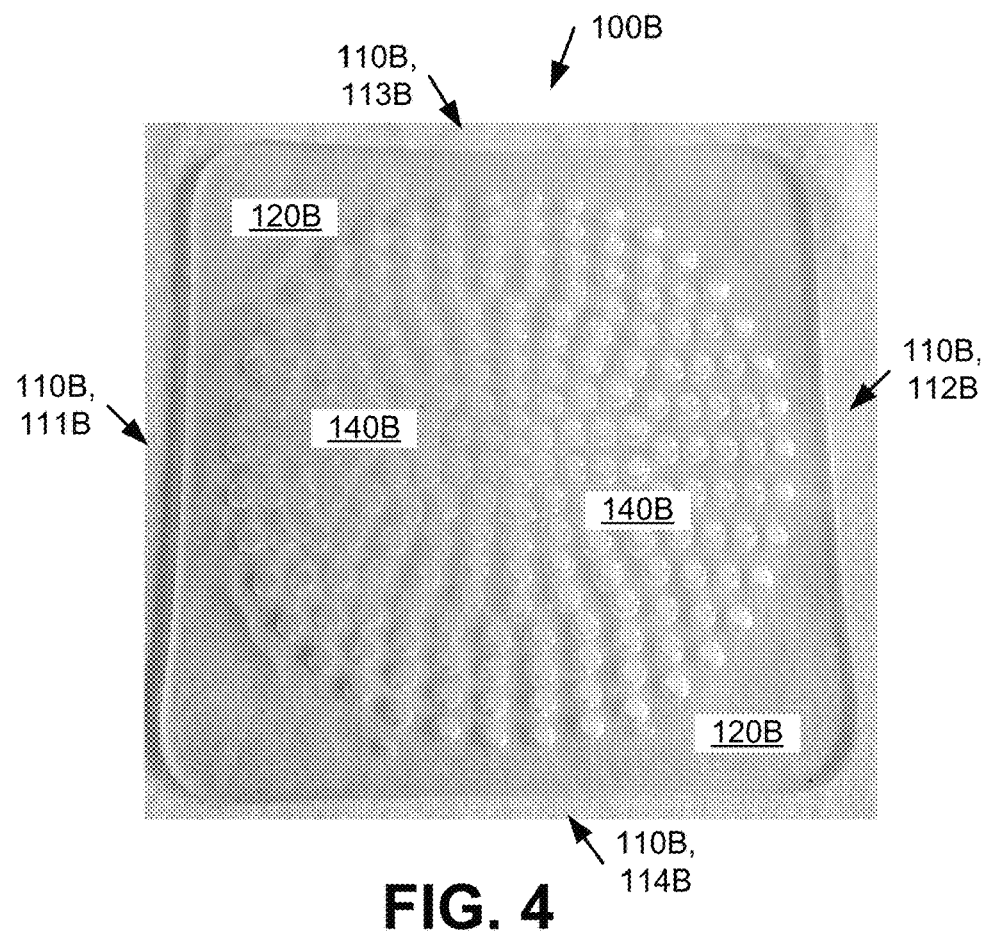
FIG. 4 illustrates another implementation of an example medical pad according to the present disclosure.

FIG. 4 illustrates another implementation of an example medical pad 100B according to the present disclosure. In some implementations, the medical pad 100B is generally the same or similar to the medical pad 100 described herein and shown in FIGS. 2A-2D. For example, as shown in FIG. 4, in some implementations, the medical pad 100B comprises a perimeter side 110B, a first surface 120B, a second surface (not shown), and a plurality of openings 140B that are generally the same or similar to the perimeter side 110, the first surface 120, the second surface 130, and the plurality of openings 140 of the medical pad 100.

Furthermore, in some implementations, the medical pad 100B is configured to prevent the development of bed sores and to help the treatment and/or healing of existing bed sores the same or similar to the medical pad 100.

Figure 5B:
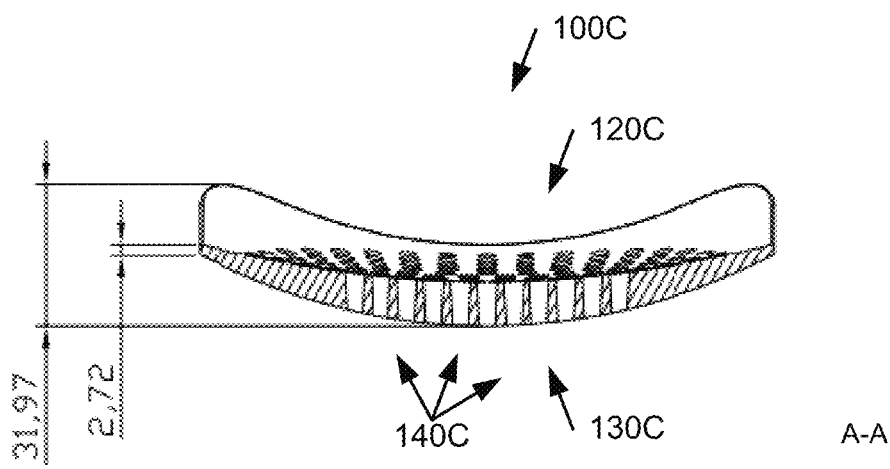

FIGS. 5A and 5B illustrate example dimensions of an example medical pad 100C according to the present disclosure. In some implementations, the medical pad 100C is generally the same or similar to the medical pad 100 described herein and shown in FIGS. 2A-2D. For example, as shown in FIGS. 5A and 5B, in some implementations, the medical pad 100C comprises a perimeter side 110C, a first surface 120C, a second surface 130C, and a plurality of openings 140C that are generally the same or similar to the perimeter side 110, the first surface 120, the second surface 130, and the plurality of openings 140 of the medical pad 100.

Furthermore, in some implementations, the medical pad 100C is configured to prevent the development of bed sores and to help the treatment and/or healing of existing bed sores the same or similar to the medical pad 100.

FIGS. 6A and 6B illustrate another implementation of an example medical pad 100D according to the present disclosure. In some implementations, the medical pad 100D is generally the same or similar to the medical pad 100 described herein and shown in FIGS. 2A-2D, except that the medical pad 100D is generally circular shaped. For example, as shown in FIGS. 6A and 6B, in some implementations, the medical pad 100D comprises a perimeter side 110D, a first surface 120D, a second surface 130D, and a plurality of openings 140D that are generally the same or similar to the perimeter side 110, the first surface 120, the second surface 130, and the plurality of openings 140 of the medical pad 100.

Furthermore, in some implementations, the medical pad 100D is configured to prevent the development of bed sores and to help the treatment and/or healing of existing bed sores the same or similar to the medical pad 100.

FIG. 7 illustrates another implementation of an example medical pad 100E according to the present disclosure. In some implementations, the medical pad 100E is generally the same or similar to the medical pad 100 described herein and shown in FIGS. 2A-2D, except that the medical pad 100E is generally circular shaped. For example, as shown in FIG. 4, in some implementations, the medical pad 100E comprises a perimeter side 110E, a first surface 120E, a second surface (not shown), and a plurality of openings 140E that are generally the same or similar to the perimeter side 110, the first surface 120, the second surface 130, and the plurality of openings 140 of the medical pad 100.

Furthermore, in some implementations, the medical pad 100E is configured to prevent the development of bed sores and to help the treatment and/or healing of existing bed sores the same or similar to the medical pad 100.

Figure 8B:
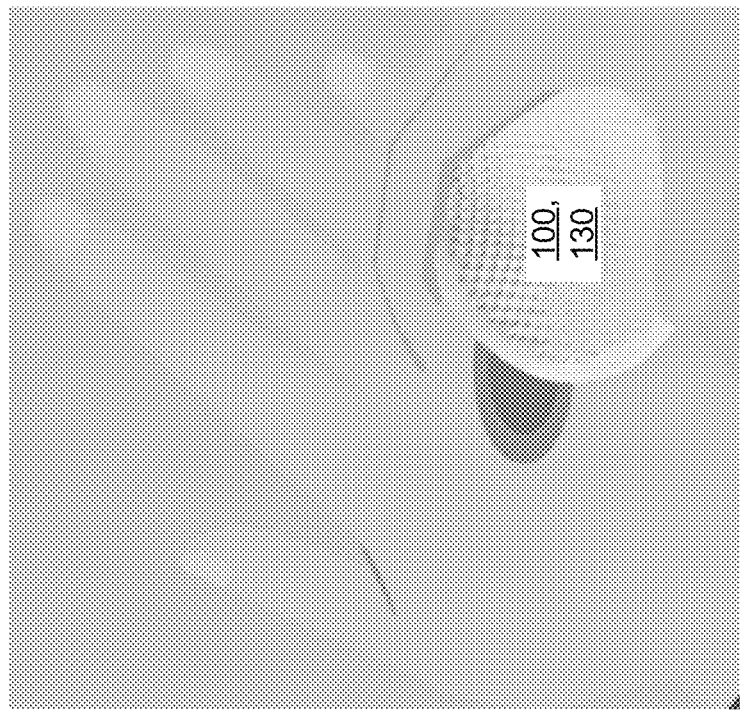
FIGS. 8A-8D illustrate an example use of the medical pad according to the present disclosure.
Figure 8A:
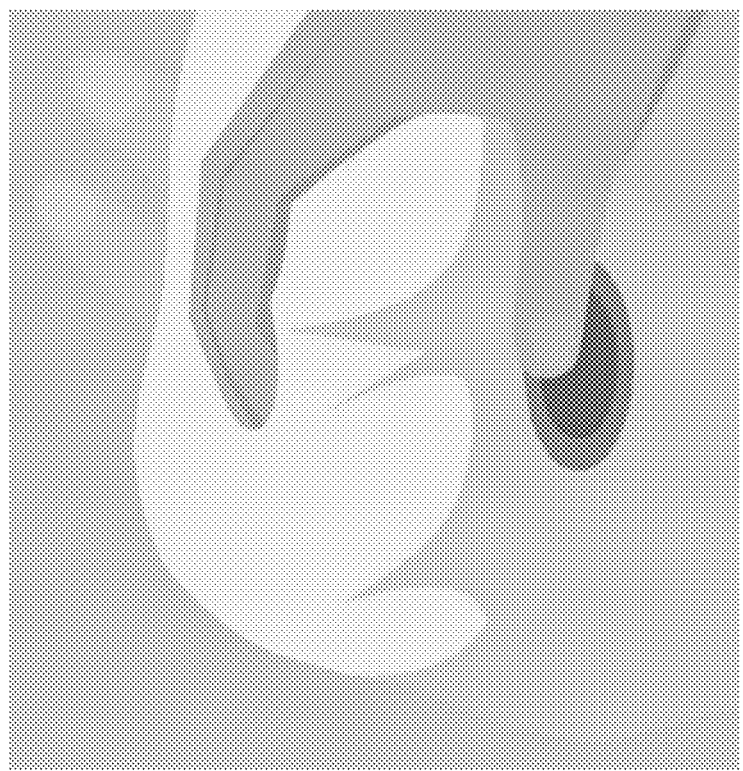
Figure 8D:
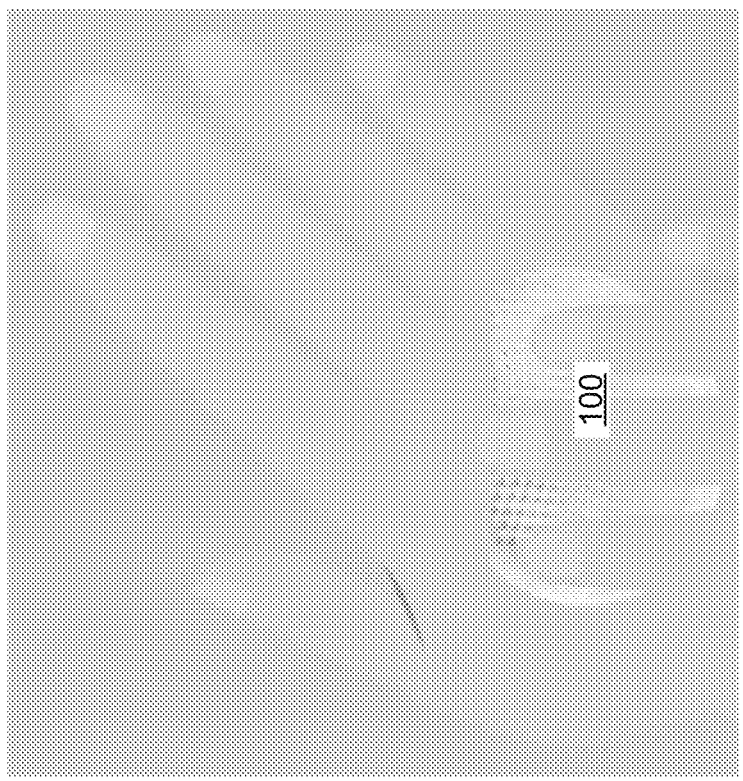
Figure 8C:
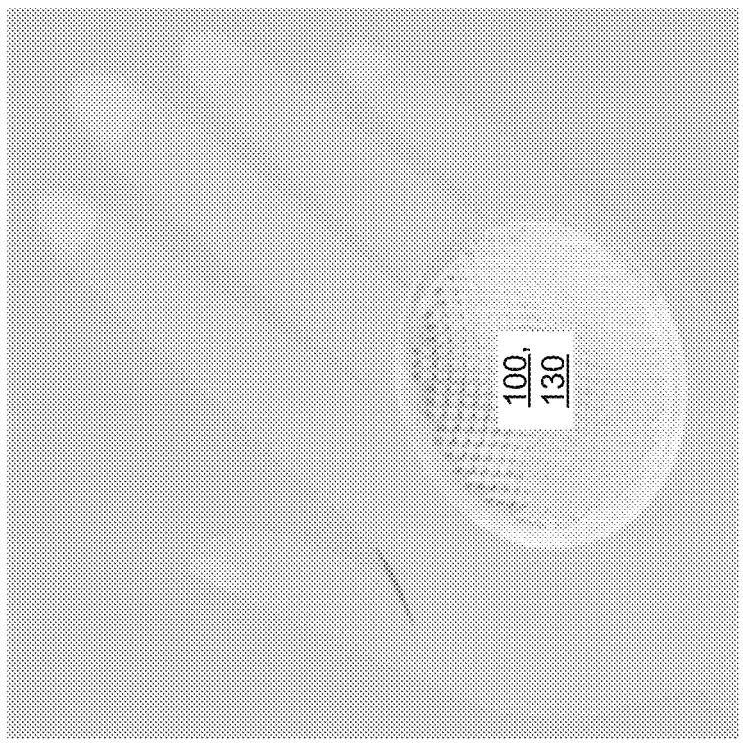

FIGS. 8A-8D illustrate an example use of the medical pad 100 according to the present disclosure. In some implementations, the medical pad 100 can be used for preventive care, such as to prevent skin breakdown and/or the development of a bedsore at a bony prominence or pressure point of a user or to allow the healing of the start of a bedsore on a user. As shown in FIGS. 8B and 8C, in some implementations, a method for using the medical pad 100 for such preventive care comprises placing (e.g., positioning) the medical pad 100 on the pressure point or other relevant position on the user (such as described for FIG. 1A).

In some implementations, the medical pad 100 is placed directly on or adjacent to the user's skin. In some implementations, the first surface 120 of the medical pad 100 is placed on or adjacent to the user's skin.

In some implementations, the medical pad 100 is applied to the user such that the medical pad 100 adheres to the user's skin. In some implementations, the applied medical pad 100 reduces or prevents skin breakdown and the development of a bed sore.

In some implementations, the method further comprises cleaning the position on the user before placing the medical pad 100 on the position, such as shown in FIG. 8A. In some implementations, the position is cleaned by washing and/or drying the position.

In some implementations, the method may further comprise any other suitable actions.

In some implementations, the medical pad 100 can be used for treatment and/or healing of an existing (i.e. already developed) bedsore that may include an open wound. In some implementations, a method for using the medical pad 100 for such treatment and/or healing comprises allowing the wound to be treated as needed to include covering the wound with a bandage, dressing, or other suitable covering. For example, in some implementations, a wound care specialist may first be consulted for treatment, bandaging, etc. of the wound.

In some implementations, the method comprises placing (e.g., positioning) the medical pad 100 on the covered wound, similar to as described above for FIGS. 8B and 8C. In some implementations, the medical pad 100 is applied to the user such that the medical pad 100 adheres to the covered wound.

In some implementations, the applied medical pad 100 helps the treatment and/or healing of the covered wound. In some implementations, the method may further comprise any other suitable actions.

As shown in FIG. 8D, in some implementations, a method of removing the medical pad 100 comprises pulling away the medical pad 100 from the placement on the user as needed. For example, in some implementations, the medical pad 100 is gradually pulled and/or rolled away on one side of the medical pad 100. In some implementations, the medical pad 100 is then pulled and/or rolled away on another (e.g. opposite) side of the medical pad 100 to gradually remove the medical pad 100 from the user's skin or covered wound.

The figures, including photographs and drawings, comprised herewith may represent one or more implementations of the medical pad.

Details shown in the figures, such as dimensions, descriptions, etc., are exemplary, and there may be implementations of other suitable details according to the present disclosure.

Reference throughout this specification to "an embodiment" or "implementation" or words of similar import means that a particular described feature, structure, or characteristic is comprised in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations may be depicted in the drawings in a particular order, this should not be understood as requiring that such operations be performed in the particular order shown or in sequential order, or that all illustrated operations be performed, to achieve desirable results.

The invention claimed is:

1. An article of manufacture comprising:
a piece of material having a perimeter side, a first surface, a second surface, and one or more openings, the piece of material forming a medical pad configured to allow treatment and healing of bedsores and to prevent development of bedsores wherein:
the piece of material is sized and shaped to position on a bedsore or an area susceptible to the development of a bedsore;
the perimeter side defines the perimeter of the piece of material extending between the first and second surfaces and has a rectangular shape;
the first and second surfaces extend opposite to each other between the perimeter side in a concave shaped portion that extends between portions adjacent to the perimeter side of the piece of material such that the first surface has a concave shape extending between portions adjacent to the perimeter side of the piece of material such that the first surface has a concave shape extending in a direction towards the second surface and the second surface has a concave shape extending between portions adjacent to the perimeter side of the piece of material such that the second surface has a concave shape extending in a direction away from the first surface, wherein the concave shaped portion is sized and shaped to position over a bedsore or an area susceptible to the development of a bedsore;
the one or more openings are positioned within the concave shaped portion and the one or more openings extend between and through the first and second surfaces;
the one or more openings are sized and shaped to allow air and vapor to pass through the one or more openings such that a bedsore or an area susceptible to the development of a bedsore can breathe while covered by the piece of material; and
the piece of material comprises a silicone material or a silicone gel material such that the concave portion is flexible.

2. A method of using the article of manufacture of claim 1 comprising positioning the piece of material on an area susceptible to the development of a bedsore such that the first surface faces toward the area and the concave shaped portion positions over the area such that the piece of material covers the area.

3. The method of claim 2 wherein positioning the piece of material on an area susceptible to the development of a bedsore comprises positioning the piece of material on a bony prominence or a pressure point.

4. The method of claim 2 wherein positioning the piece of material on an area susceptible to the development of bedsore comprises positioning the piece of material on the back of the head, a shoulder, an elbow, a hip, the lower back, an inner knee, or a heel.

5. The method of claim 2 further comprising removing the piece of material from the area susceptible to the development of a bedsore.

6. A method of using the article of manufacture of claim 1 comprising positioning the piece of material on a bedsore such that the first surface faces toward the bedsore and the concave shaped portion positions over the bedsore such that the piece of material covers the bedsore.

7. The method of claim 6 wherein the bedsore is covered with a dressing and the piece of material is positioned on the bedsore over the dressing.

8. The method of claim 6 further comprising removing the piece of material from the bedsore.

9. The article of manufacture of claim 1 wherein the piece of material has a length and a width of about 5 inches and a thickness between the first surface and the second surface of about 0.4 inches.

10. The article of manufacture of claim 1 wherein the piece of material weighs about 150 grams.

11. The article of manufacture of claim 1 wherein the piece of material further comprises an adhesive configured such that the piece of material is adherable and removable from adherence to skin of a user when the piece of material is positioned on a bedsore or an area susceptible to the development of a bedsore.

12. The article of manufacture of claim 1 wherein the piece of material is further sized and shaped to provide shock absorption that protects a bedsore or an area susceptible to the development of a bedsore from external force when the piece of material is positioned on the bedsore or the area susceptible to the development of a bedsore.

13. The article of manufacture of claim 1 wherein a height of the concave shaped portion of the piece of material is about 2 inches.

14. The article of manufacture of claim 1 wherein the one or more openings are about 3.6 millimeters wide.

15. The article of manufacture of claim 1 wherein the piece of material is sized and shaped to position on a bony prominence or a pressure point.

16. The article of manufacture of claim 1 wherein the piece of material is sized and shaped to position on the back of the head, a shoulder, an elbow, a hip, the lower back, an inner knee, or a heel.

* * * * *